(12) United States Patent
Klingenbeck-Regn

(10) Patent No.: US 7,558,368 B2
(45) Date of Patent: Jul. 7, 2009

(54) METHOD FOR CREATION OF STEREO IMAGE PAIRS OF AN OBJECT UNDER EXAMINATION WITH AN X-RAY SYSTEM AND X-RAY SYSTEM

(75) Inventor: Klaus Klingenbeck-Regn, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 1 day.

(21) Appl. No.: 11/888,207

(22) Filed: Jul. 31, 2007

(65) Prior Publication Data
US 2008/0031411 A1 Feb. 7, 2008

(30) Foreign Application Priority Data
Aug. 3, 2006 (DE) ........................ 10 2006 036 281

(51) Int. Cl.
*A61B 6/02* (2006.01)
(52) U.S. Cl. .......................................... 378/41; 378/62
(58) Field of Classification Search .................. 378/41, 378/62, 197, 196
See application file for complete search history.

(56) References Cited

U.S. PATENT DOCUMENTS

| 4,807,273 | A | | 2/1989 | Haendle | |
|---|---|---|---|---|---|
| 5,163,076 | A | * | 11/1992 | Koyama | 378/42 |
| 6,862,364 | B1 | * | 3/2005 | Berestov | 382/132 |
| 6,869,217 | B2 | * | 3/2005 | Rasche et al. | 378/197 |
| 7,298,816 | B2 | * | 11/2007 | Moore et al. | 378/37 |

FOREIGN PATENT DOCUMENTS

| DE | 29 43 700 C2 | 5/1980 |
|---|---|---|
| DE | 34 37 203 A1 | 4/1986 |
| DE | 36 36 678 A1 | 5/1988 |
| DE | 42 30 975 A1 | 3/1994 |
| DE | 10 2005 012 700 A1 | 9/2006 |

* cited by examiner

*Primary Examiner*—Hoon Song

(57) ABSTRACT

To guarantee the ability to create stereo image pairs in real time, the invention relates a method for creating stereo image pairs of an object under examination with an x-ray system, featuring a recording unit comprising an x-ray detector and an x-ray source, with said recording unit being carried by an industrial robot and being able to be rotated around a center of rotation or around an axis of rotation is provided, in which a first x-ray image of the object under examination is recorded at a first angle of rotation of the recording unit around a center of rotation or an axis of rotation and subsequently a second x-ray image of the object under examination is recorded at a second angle of rotation of the recording unit around the center of rotation or the axis of rotation.

15 Claims, 3 Drawing Sheets

METHOD FOR CREATION OF STEREO IMAGE PAIRS OF AN OBJECT UNDER EXAMINATION WITH AN X-RAY SYSTEM AND X-RAY SYSTEM

CROSS REFERENCE TO RELATED APPLICATIONS

This application claims priority of German application No. 10 2006 036 281.0 filed Aug. 3, 2006, which is incorporated by reference herein in its entirety

FIELD OF THE INVENTION

The invention relates to a method for creating stereo image pairs of an object under examination with an x-ray system and to an x-ray system for executing such a method.

BACKGROUND OF THE INVENTION

The recording of pairs of x-ray stereo images of objects under examination is known from x-ray imaging to enable as spatial a presentation as possible of the objects under examination to be obtained. These types of stereo image pairs are formed from two so-called half images of the same object displaced sideways from each other, which are recorded as simultaneously as possible. The spatial distance between the two half images in such cases generally amounts to at least around 5° to 10°. An observer who uses anaglyphic eyeglasses to view the pairs of stereo images recorded in overlay obtains a spatial impression of the object under examination.

Recording the two half images by means of a stereoscopic x-ray tube featuring at least two x-ray focuses spaced from each other is known for example from DE 29 43 700 C2. In this case the spacing between the x-ray foci is fixed and cannot be varied. The use of two different x-ray tubes for recording the two half images is known from DE 42 30 975 A1. In this case simultaneous recording is possible, but two x-ray tubes are needed and the arrangement is not flexible. An x-ray diagnostic device for mammography is known from DE 34 37 203 C2, in which the X-ray tube is supported to allow adjustment between two end positions for the recording of the two half images. In the method for recording the half images the x-ray tubes are adjusted manually here between two recordings, which does not allow a rapid succession of recordings to be made. Some effort is also involved is changing this arrangement.

SUMMARY OF THE INVENTION

The object of the present invention is to provide a method for creation of stereo image pairs of an object under examination with an x-ray system which is also able to be executed flexibly and in real time with a single x-ray focus; furthermore it is an object of the invention to provide a suitable x-ray system for executing the method.

The object is achieved in accordance with the invention by a method for creating pairs of stereo images of an object under examination with an x-ray system and by an x-ray system in accordance with the claims. Advantageous embodiments of the invention are the subject matter of the dependent claims in each case.

The invention uses the flexibility of an x-ray system, of which the recording unit comprises an x-ray detector and an x-ray source carried by an industrial robot and consequently able to be rotated around a center of rotation arranged at any point or around an axis or rotation, in order to create with the recording unit in rapid sequence a first x-ray image at a first angle of rotation and a second x-ray image at a second angle of rotation. The assumption of these two positions, i.e. the rotation around the center of rotation or the axis of rotation, can be controlled simply and at low cost by this type of x-ray system. The two x-ray images can then be overlaid and combined into a stereo image in a simple manner. A rotation of the recording system from a first angle of rotation into a second angle of rotation is possible by means of the industrial robot which reaches angular speeds of for example 100°/s, with a 5° difference between the first and the second angle of rotation possible in 0.05 s.

In accordance with an embodiment of the invention the center of rotation or the axis of rotation lies in the plane of the x-ray detector, in particular the center of rotation is formed by center point of the x-ray detector or the axis of rotation intersects the center point of the x-ray detector. The two x-ray images determined give a particularly good spatial impression since the position of the x-ray detector is not shifted but the detector is merely tilted.

In an advantageous manner the recording unit is rotated between the recording of the first x-ray image and the recording of the second x-ray image by a relative angle of rotation, which amounts to the difference between the first and the second angle of rotation, around the center point of the x-ray detector or an axis of rotation intersecting this point. According to a further embodiment of the invention, the recording unit, after the recording of the second x-ray image, is rotated back by relative angle of rotation around the center point of the x-ray detector or the axis of rotation through the center point of the x-ray detector into the position of the first x-ray image, so that further pairs of stereo images can be recorded in a simple manner.

In an advantageous manner, for an especially authentic stereo impression closely approximating to the interpupillary distance, the relative angle of rotation is between 5° and 10°.

To obtain a real-time impression of the object under examination in a stereo representation, a plurality of stereo image pairs of an object under examination is advantageously created at a first and a second angle of rotation respectively. In accordance with an embodiment of the invention at least eight stereo image pairs per second, especially between ten and twenty stereo image pairs per second are created, in order to obtain an especially good real time representation.

Expediently the stereo image pair or the sequence of stereo image pairs is displayed on an image display unit.

An x-ray system especially suitable for executing the inventive method in this case is an x-ray system with a recording unit comprising an x-ray detector and an x-ray source, with the recording unit being mounted on a C-arm and the C-arm carried by an industrial robot.

BRIEF DESCRIPTION OF THE DRAWINGS

The invention along with further advantageous embodiments in accordance with features of the subclaims, are explained in greater detail below with reference to schematic exemplary embodiments in the drawing, without the invention being thus restricted to these exemplary embodiments; the figures show:

DETAILED DESCRIPTION OF THE INVENTION

Figure 1:
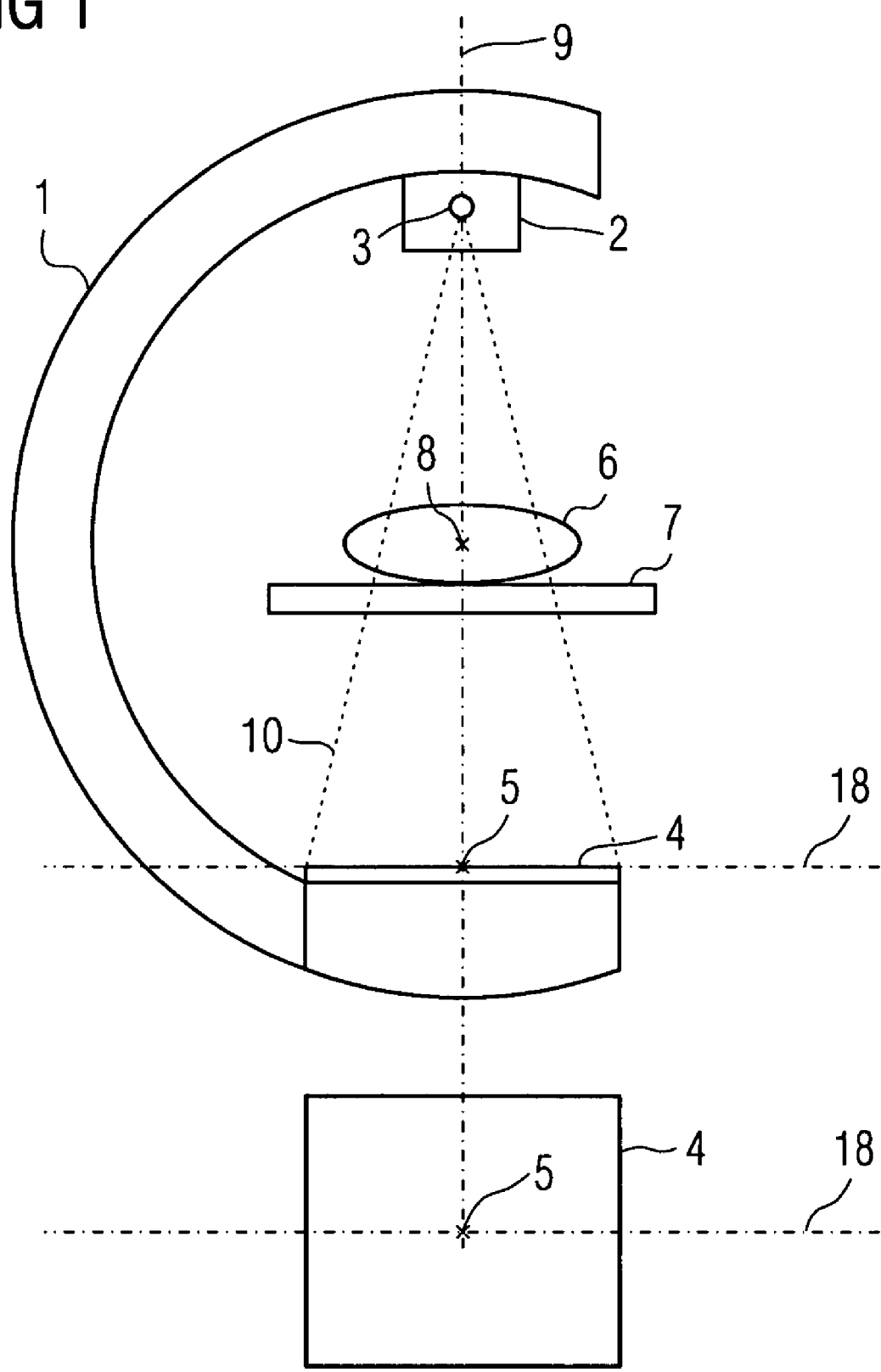
FIG. 1 a front view of a C-arm with an x-ray source and a x-ray detector.
Figure 2:
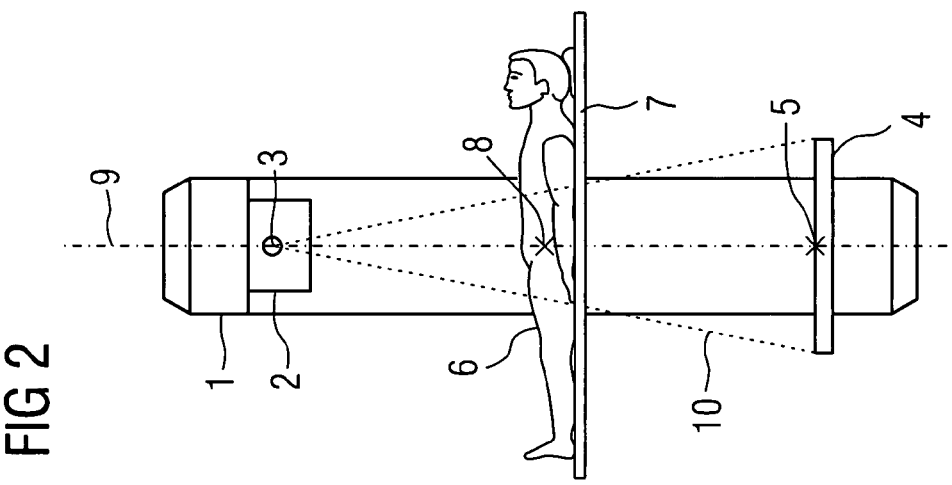
FIG. 2 a side view of a C-arm with an x-ray source and an x-ray detector.

FIG. 1 and FIG. 2 shown schematic diagrams of a C-arm 1 of an x-ray system with an x-ray source 2 and an x-ray detector 4, viewed from above (FIG. 1) and in a side view (FIG. 2). A patient bed 7 with an object under examination 6 supported on it is disposed between the x-ray source 2 and the x-ray detector 4, which are both fixed at different ends of the C-arm. The x-ray source 2 creates an x-ray beam 10 which has its origin in a focus 3.

The x-ray beam 10 illuminates the object under examination 6 or the area to be investigated of the object under examination 6. In general the object under examination 6 is positioned such that the center point 8 of the area to be examined is intersected by an axis of balance 9, which is formed by a plumb line of the focus 3 onto the center point 5 of the x-ray detector 4 in the initial position of the C-arm. The center point 5 of the x-ray detector 4 in this case is to be understood as the center point of the detector surface. The C-arm 1 is arranged to allow rotation around a center of rotation and/or an axis of rotation.

Figure 6:
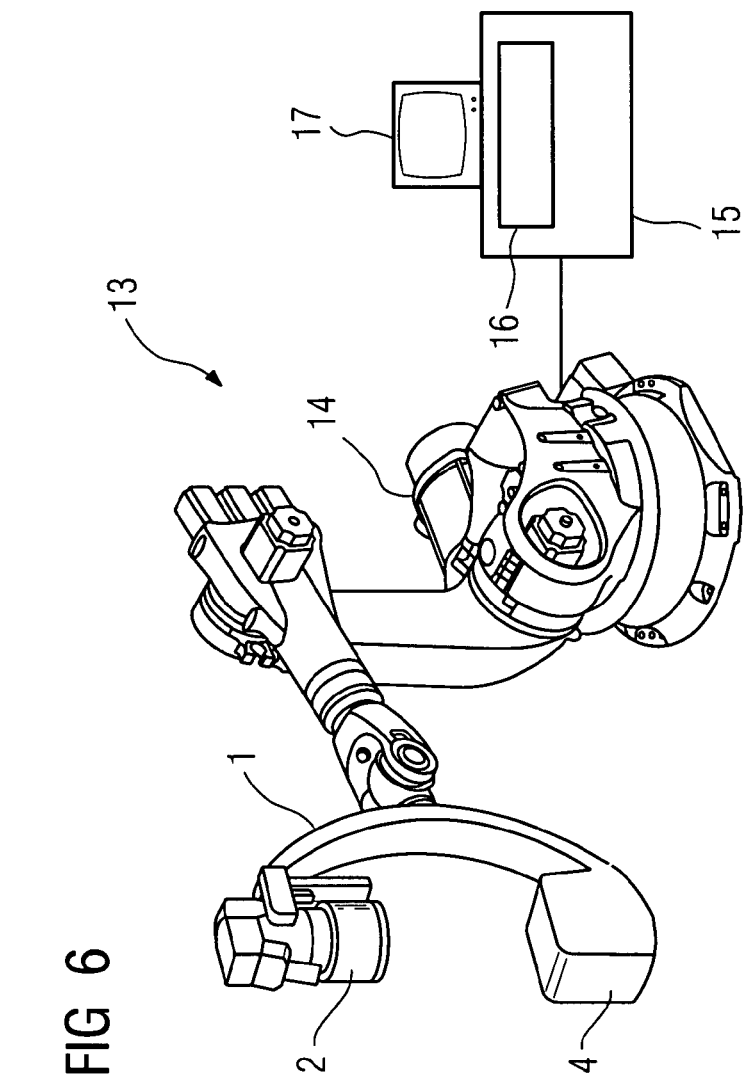
FIG. 6 an inventive x-ray system with an industrial robot holding a C-arm.

FIG. 6 shows a inventive x-ray system 13, which features an industrial robot 14 which carries the C-arm 1. The x-ray system 13 is controlled by a system controller 15, recorded x-ray images are processed by an image system 16 and can be displayed on an image display unit 17.

By means of the Industrial robot 14, which preferably features six axes of rotation and thereby six degrees of freedom (known from the non-published German Patent Application 10 2005 012 700.2), the C-arm 1 can be adjusted to any given spatial position, for example by being rotated around a center of rotation between the focus 3 and (inclusive) the x-ray detector 4. The inventive x-ray system 13 is especially able to be rotated around centers of rotation and axes of rotation in the plane of the x-ray detector 4, preferably around the center point 5 of the x-ray detector 4 and around the center point 5 of the axes of rotation intersecting the x-ray detector 4, such as the axis of rotation 18 lying in the C-arm plane. FIG. 1 also shows an overhead view for clarification, that is a view form the x-ray source 2 onto the x-ray detector 4, of which the center point and the axis of rotation intersecting the center point 5 lying in the C-arm plane.

Figure 4:
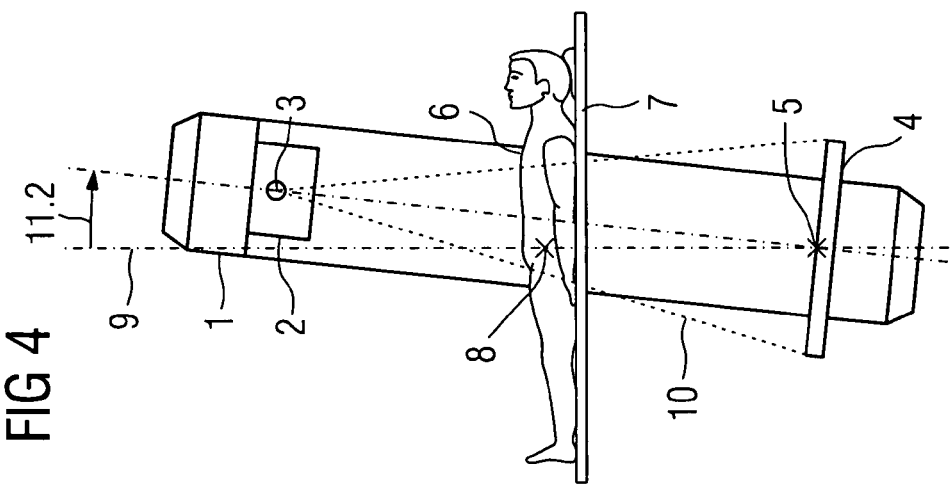
FIG. 4 a side view of the C-arm depicted in FIG. 2 in a further rotated position for recording a second half image for the inventive method.
Figure 3:
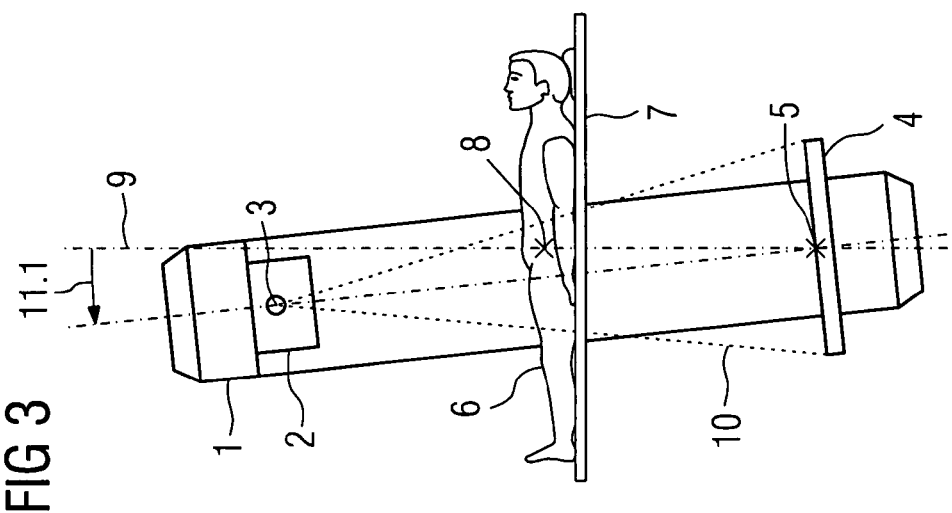
FIG. 3 a side view of the C-arm depicted in FIG. 2 in a rotated position for recording of a first half image for the inventive method.
Figure 5:
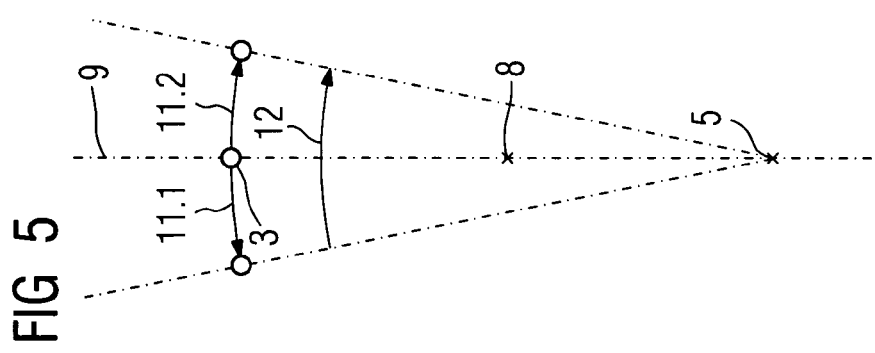
FIG. 5 a geometrical view of the two angles of rotation and of the relative angle of rotation.

FIG. 3 and FIG. 4 show the C-arm 1 in two different positions, which differ by an angle of rotation of the recording system around the axis of rotation 18 lying in the C-arm plane through the center point 5 of the x-ray detector 4. The axis of rotation 18 lies in this case in the plane spanned by the C-arm. In FIG. 3 the C-arm is rotated by a first angle of rotation 11.1 in relation to its rest position and in FIG. 4 the C-arm 1 is rotated by a second angle of rotation 11.2 in relation to its rest position, so that overall a relative angle of rotation 12 is produced from the difference between the amount of the first angle of rotation and that of the second angle of rotation. The geometrical relationships are shown in FIG. 5.

The two half images required for a spatial impression of the area to be examined are recorded in sequence in the inventive method. Initially a first x-ray image is recorded, in which the recording system is rotated by the first angle of rotation 11.1 and subsequently a second x-ray image is recorded, in which the recording system is rotated by the second angle of rotation 11.2.

Between the recording of the first x-ray image and the recording of the second x-ray image the C-arm is rotated or tilted around the axis of rotation 18 through the center point 5 of the x-ray detector arranged in the C-arm of the x-ray detector 4 by the relative angle of rotation 12. If more than one pair of stereo images is recorded, after the recording of the second x-ray image the C-arm 1 is rotated back by the relative angle of rotation 12, so that the first position is assumed again and a further stereo image pair can be created.

The C-arm 1 moved by the industrial robot 14 allows rotations at an angular speed of for example 100°/s. If the relative angle of rotation 12 amounts to 5 degrees for example, then up to 10 pairs of images can be recorded in one second.

An axis of rotation around which the C-arm 1 is rotated or tilted can also for example lie orthogonally or at another angle to the C-arm plane, provided it lies in the plane of the x-ray detector 4 and especially runs through the center point 5 of the x-ray detector.

After the recording of the respective stereo image pair the respective first x-ray image and the respective second x-ray image, i.e. the two respective half images, are converted into a stereo image in a known manner for example by the image system 16 by overlaying and are presented for display on the image display unit 17 or stored.

The invention can be briefly summarized as follows: To ensure that pairs of stereo images can also be created in real time a method for creating pairs of stereo images of an object under examination is provided, with an x-ray system featuring a recording unit comprising an x-ray detector and an x-ray source, with the recording unit being mounted on an industrial robot and able to be rotated around a center of rotation or an axis of rotation, in which a first x-ray image of the object under examination is recorded at a first angle of rotation of the recording unit around a center of rotation or an axis of rotation and subsequently a second x-ray image of the object under examination is recorded at a second angle of rotation of the recording unit around the center of rotation or the axis of rotation.

The invention claimed is:

1. A method for creating a stereo x-ray image pair of an object by a recording unit with an x-ray source and an x-ray detector, comprising:
   mounting the recording unit on an industrial robot;
   rotating the recording unit around an axis of rotation to a first angle of rotation;
   recording a first x-ray image of the object at the first angle of rotation;
   subsequently rotating the recording unit around the axis of rotation to a second angle of rotation;
   recording a second x-ray image of the object at the second angle of rotation; and
   creating the stereo x-ray image pair of the object based on the first and the second x-ray images for a spatial impression of the object,
   wherein the recording unit is rotated around a center of rotation, and
   wherein the center of rotation or the axis of rotation is in a plane of the x-ray detector.

2. The method as claimed in claim 1, wherein the center of rotation or the axis of rotation is a center point of the x-ray detector or intersects the center point of the x-ray detector.

3. The method as claimed in claim 1, wherein the recording unit is rotated between the recording of the first and the second x-ray images by a relative angle of rotation.

4. The method as claimed in claim 3, wherein the relative angle of rotation is a difference between the first angle of rotation and the second angle of rotation.

5. The method as claimed in claim 4, wherein the relative angle of rotation is between 5° and 10°.

6. The method as claimed in claim 1, wherein the recording unit is rotated back into the first angle of rotation after the recording of the second x-ray image.

7. The method as claimed in claim 1, wherein with the recording unit is mounted on a C-arm and the C-arm is carried by the industrial robot.

8. The method as claimed in claim 1, wherein a plurality of stereo x-ray image pairs are created respectively at the first and the second angles of rotation.

9. The method as claimed in claim 8, wherein at least eight stereo x-ray image pairs are created per second.

10. The method as claimed in claim 9, wherein between ten and twenty stereo x-ray image pairs are created per second.

11. The method as claimed in claim 1, wherein the stereo x-ray image pair is created by overlaying the first and the second x-ray images.

12. The method as claimed in claim 1, wherein the stereo x-ray image pair is displayed on an image display unit.

13. An x-ray system, comprising:
a recording unit comprising an x-ray source and an x-ray detector; and
an industrial robot for supporting the recording unit that:
rotates the recording unit around an axis of rotation to a first angle of rotation so that the recording unit records a first x-ray image of an object at the first angle of rotation, and
subsequently rotates the recording unit around the axis of rotation to a second angle of rotation so that the recording unit records a second x-ray image of the object at the second angle of rotation,
wherein the recording unit is rotated around a center of rotation, and
wherein the center of rotation or the axis of rotation is in a plane of the x-ray detector,
further comprising an image system that creates a stereo x-ray image pair of the object by overlaying the first and the second x-ray images of the object.

14. The x-ray system as claimed in claim 13, wherein the center of rotation or the axis of rotation is a center point of the x-ray detector or intersects the center point of the x-ray detector.

15. The x-ray system as claimed in claim 13, wherein the recording unit is mounted on a C-arm and the C-arm is carried by the industrial robot.

* * * * *